United States Patent

Moshe et al.

[19]

[11] Patent Number: 5,845,529
[45] Date of Patent: Dec. 8, 1998

[54] DEVICE AND METHOD FOR DETERMINING THE MOISTURE CONTENT OF MATERIAL

[75] Inventors: Danny S. Moshe, Kiryat Ono; Alexander Greenwald, Nazareth-Illit, both of Israel

[73] Assignee: Malcam Ltd., Nazareth-Illit, Israel

[21] Appl. No.: 777,872

[22] Filed: Dec. 31, 1996

Related U.S. Application Data

[63] Continuation-in-part of Ser. No. 503,838, Jul. 18, 1995, Pat. No. 5,621,330.

[51] Int. Cl.⁶ ..................................................... G01N 5/02
[52] U.S. Cl. .............................................. 73/73; 324/640
[58] Field of Search ................... 73/73, 29.01; 324/640, 324/643

[56] References Cited

U.S. PATENT DOCUMENTS

| | | |
|---|---|---|
| 2,659,860 | 11/1953 | Breazeale . |
| 3,360,721 | 12/1967 | Pullman . |
| 3,644,826 | 2/1972 | Cornetet, Jr. . |
| 3,810,005 | 5/1974 | Bennion et al. .................... 324/58.5 A |
| 3,815,019 | 6/1974 | Wiles ................................. 324/58.5 A |
| 3,829,764 | 8/1974 | Bosisio ................................. 324/58 R |
| 4,123,702 | 10/1978 | Kinanen et al. .................... 324/58.5 A |
| 4,353,059 | 10/1982 | Suh et al. ............................... 324/61 R |
| 4,361,801 | 11/1982 | Meyer et al. ....................... 324/58.5 R |
| 4,500,835 | 2/1985 | Heikkila ............................. 324/58.5 R |
| 4,546,311 | 10/1985 | Knöchel .............................. 324/58.5 R |
| 4,578,998 | 4/1986 | Gard . |
| 4,675,595 | 6/1987 | Hane ....................................... 324/58.5 |
| 4,789,820 | 12/1988 | Parrent et al. ..................... 324/58.5 R |
| 4,962,384 | 10/1990 | Walker ..................................... 343/786 |
| 4,991,915 | 2/1991 | Thompson et al. ..................... 324/640 |
| 5,333,493 | 8/1994 | Cutmore . |
| 5,581,191 | 12/1996 | Yamaguchi ............................. 324/637 |
| 5,619,143 | 4/1997 | Stevens et al. ......................... 324/639 |

*Primary Examiner*—Hezron E. Williams
*Attorney, Agent, or Firm*—Mark M. Friedman

[57] ABSTRACT

A device for measuring the moisture content of a module of material, including: (a) a source of microwave radiation for producing a microwave radiation source beam, at least a portion of the source being located on one side of the module; (b) at least one microwave antenna located on an opposing side of the module for receiving an exit beam and for producing an antenna signal, the exit beam being the source beam after a transition from the source to the antenna; (c) an attenuation unit for receiving a first portion of the antenna signal and for measuring an attenuation of the antenna signal; (d) a phase shift determiner for receiving a portion of the source beam and a second portion of the antenna signal and for determining a phase shift of the source beam and the antenna signal, the phase shift determiner including: (i) a raw phase shift measurer for determining a raw phase shift of the source beam and the antenna signal; and (ii) a phase region determiner for determining a phase region of the raw phase shift from the attenuation and producing a corrected phase shift; and (e) a moisture determiner for determining a moisture content of the module from the corrected phase shift and the attenuation.

13 Claims, 9 Drawing Sheets

FIG. 3
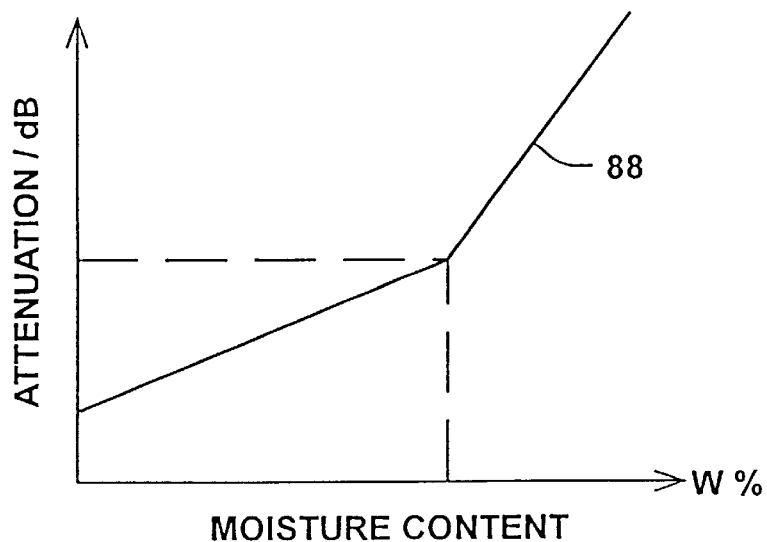
FIG. 4A
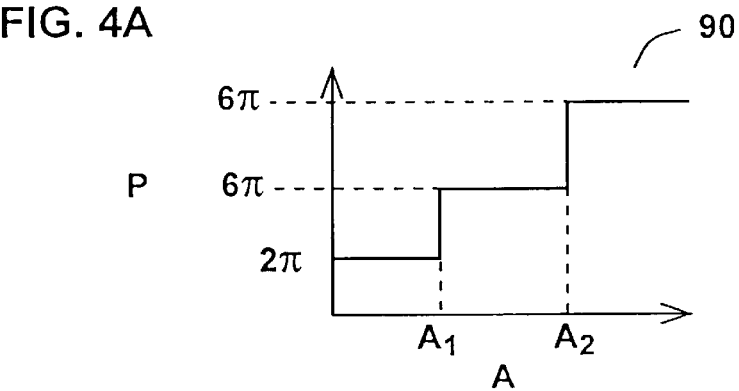
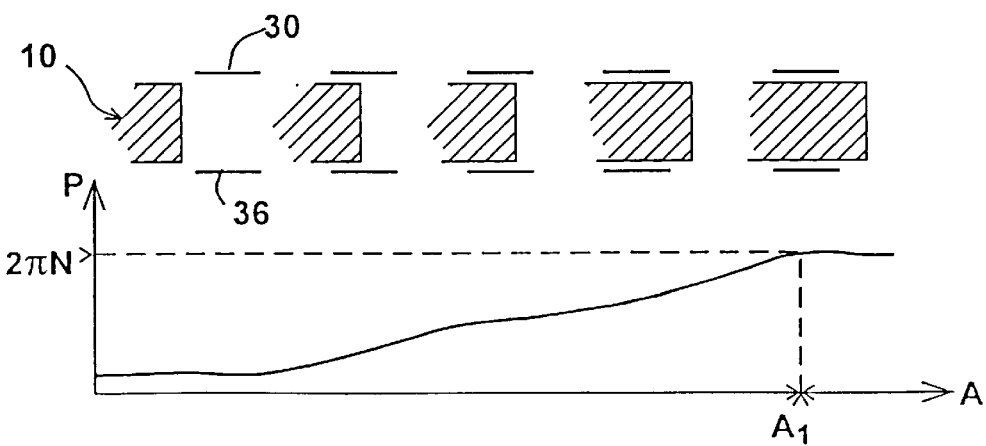
FIG. 4B

DEVICE AND METHOD FOR DETERMINING THE MOISTURE CONTENT OF MATERIAL

This application is CIP of Ser. No. 08/503,838 U.S. Pat. No. 5,621,330.

FIELD AND BACKGROUND OF THE INVENTION

The present invention relates to a device and method for determining the moisture content of material with multiple layers and, more particularly, to a device and method for determining the moisture content of non-homogeneous material.

Many different types of synthetic and organic material are the basis for the construction of many different manufactured products. These materials must be gathered, transported and stored before being used in the manufacturing process. The manufacturing process itself may require multiple procedures, first to prepare the raw material, and then to use the processed material in the formation of the actual product. Many of these procedures are dependent upon the moisture content of the material. If the moisture content is too high, for example, the material may decompose during storage and transportation, before it can be used. If the moisture content is too low, processing and use of the material may be difficult.

Synthetic and organic materials whose behavior depends upon their moisture content include tobacco, cotton, paper, processed wood, tea and synthetic fibers. As an example, cotton can be considered, although it will be appreciated that similar examples could be given for any of the above materials. Raw cotton is a mixture of seeds and cotton fibers, which must be processed to separate the desired cotton fibers from the seeds. A cotton gin is used to separate the fibers from the seeds. In order for the gin to operate effectively, the moisture of the cotton fibers must be controlled during this processing. If the moisture content of the cotton fibers is too high, the fibers will tend to form wads which adhere to the cotton gin during processing, and which decompose more readily in storage. If the moisture content of the fibers is too low, the fibers will tend to generate static electricity and cling to metal surfaces. Fibers with low moisture content are also weaker, breaking more frequently.

The optimum moisture content of the cotton fibers is from 6.5 to 8%. However, the raw cotton can have a moisture content ranging from less than 3% to more than 20%. Thus, as the cotton gin processes the cotton, it must control the moisture content of the fibers to compensate for the widely varying moisture content of the raw cotton. Effective moisture control depends upon accurate measurement of the moisture content of the cotton.

Such measurements may be performed using microwave radiation. Typically, a microwave radiation source is located on one side of the cotton module, and an antenna is located on the opposite side of the cotton module. The radiation source beam is transmitted through a portion of the module and is received by the antenna, which then produces a signal. This signal is used to determine the moisture content of that portion of the module.

However, such measurements are difficult to perform, because of the size and internal structure of the raw material. Raw cotton is typically transported in massive modules. On average, each module has a width of 3 m, a height of 3 m and a length of 6 m, and a weight of 8 tons. Each module has many layers of material. Usually, these layers are somewhat loose, although they can be pressed together and bound by metal or plastic bars. Thus, a single measurement of the moisture content of the entire module is not physically possible. However, if the moisture content of only a portion of the module is measured, the moisture content of the entire module cannot be accurately determined from a single measurement because the moisture content through the module may vary from one point to another by approximately 5%. Thus, multiple measurements are required which do not damage the material itself.

The internal structure of the module itself presents difficulties. The layers of the raw cotton within the module frequently are not parallel, which can artifactually alter the behavior of the transmitted beam, and hence the apparent moisture content of the bale. Thus, the internal structure of the module must be compensated for during calculation of the moisture content of the material.

Furthermore, many types of modules can be used for transporting and storing raw cotton. Raw cotton can be transported and stored in cases. The internal structure of the case is typically less organized, leading to even greater inhomogeneities of material, and potentially causing even greater measuring artifacts. Cotton can also be transported and stored in bales. On average, each bale has a width of 0.5 m, a height of 0.7 m and a length of 1.4 m, and a weight of 250 Kg. Each bale has many layers of material which are pressed together and bound by metal or plastic bars. Thus, the internal structure of the bale is different from that of the case, so that a moisture measuring device which included compensation for the non-parallel layers of the bale would need different signal processing to compensate for the looser structure of the case.

Of course, cotton is not the only material to be transported, stored and processed. As mentioned above, tobacco, paper, processed wood, tea and synthetic fibers are also necessary synthetic and organic materials which form the basis of many different products. Each of these materials may also be transported and stored in several different forms, such as bale and case. The moisture content of each can affect processing, storage and manufacture. Furthermore, each of these materials forms different structures. That is, a bale of tobacco may have a very different internal structure from a bale of cotton. Thus, a moisture measuring device must be able to compensate for the effect of all of these different types of structures on the measured moisture content.

Unfortunately, no such moisture measuring device is known in the prior art. U.S. Pat. No. 4,578,998, for example, is designed to measure the moisture content of sheet material. However, no mention is made of compensation for the layers of material being non-parallel. Furthermore, such a device would not be suitable for material which is not organized into such structured layers, such as cotton cases.

U.S. Pat. No. 2,659,860 is designed to measure the moisture content of bales of material, by directing a microwave beam through the bale and receiving the beam with an antenna, which generates a signal. The moisture content of the bale is then determined from this signal. During this measurement, the bale must remain stationary between the source of the beam and the antenna, as described in column 5, lines 4–7. Furthermore, the bale must be carefully placed, so that the beam passes between the metal tie bars of the bale. The placement of the beam is also crucial because only a single measurement of the moisture content of the bale is made. However, the moisture content of the bale can differ by as much as five percent between two locations separated by only 2 cm, due to locally non-homogeneous material within the bale. Thus, the single measurement may not accurately reflect the overall moisture content of the bale. Furthermore, since the device does not include conveying means, or any means for making continuous or continual measurements, on a practical level making multiple measurements of the moisture content of a bale would be very difficult, since the bale would need to be manually moved for each new measurement. Finally, no mention is made of compensation for the layers of material being non-parallel, or indeed for the material not being organized into layers at all.

There is thus a widely recognized need for, and it would be highly advantageous to have, a device for measuring the moisture content of a unit of material, which can compensate for the internal structure of the unit of material, or lack thereof, which can make multiple measurements in order to determine the average moisture content of the entire unit of material, and which is capable of adjusting such measurements for the material itself.

SUMMARY OF THE INVENTION

According to the present invention there is provided a device for measuring the moisture content of a module of material, including: (a) a source of microwave radiation for producing a microwave radiation source beam, at least a portion of the source being located on one side of the module; (b) at least one microwave antenna located on an opposing side of the module for receiving an exit beam and for producing an antenna signal, the exit beam being the source beam after a transition from the source to the antenna; (c) an attenuation unit for receiving a first portion of the antenna signal and for measuring an attenuation of the antenna signal; (d) a phase shift determiner for receiving a portion of the source beam and a second portion of the antenna signal and for determining a phase shift of the source beam and the antenna signal, the phase shift determiner including: (i) a raw phase shift measurer for determining a raw phase shift of the source beam and the antenna signal; (ii) a phase region determiner for determining a phase region of the raw phase shift from the attenuation and producing a corrected phase shift; and (e) a moisture determiner for determining a moisture content of the module from the corrected phase shift and the attenuation.

According to another embodiment, there is provided a device for measuring the moisture content of a multi-layer bale of material, including: (a) a source of microwave radiation for producing a microwave radiation source beam; (b) at least one microwave antenna for receiving an exit beam and for producing an antenna signal, the exit beam being the source beam after a transition from the source to the antenna, the at least one microwave antenna being located substantially opposite the source of microwave radiation; (c) a conveyor for conveying the bale between the source of microwave radiation and the at least one microwave antenna, such that when the source beam passes through a portion of the bale, the exit beam is received by the antenna, and such that the source beam is enabled to pass through a plurality of portions of the bale; (d) a bale alignment determiner, for examining the antenna signal and determining the alignment of the bale relative to the antenna and the source of microwave radiation, the bale alignment determiner including: (i) a leading edge transition determiner, for detecting when a leading edge of the bale passes the source of microwave radiation and producing a leading edge transition signal after the leading edge has passed the source of microwave radiation; (ii) an interval timer, for producing an alignment signal after receiving the leading edge transition signal, the alignment signal being the antenna signal produced during a time interval when the bale is correctly aligned between the source of microwave radiation and the antenna; and (iii) a trailing edge transition determiner, for detecting when a trailing edge of the bale passes the source of microwave radiation and producing a trailing edge transition signal after the trailing edge has passed the source of microwave radiation; and (e) a moisture determiner for determining the moisture content of the bale from the alignment signal and for determining a background moisture content after receiving the trailing edge transition signal, the moisture determiner including: (i) a filter for producing a corrected signal by removing the background moisture content from the alignment signal; and (ii) a mean moisture unit for computing the moisture content of the bale from the corrected signal.

According to another embodiment, there is provided a method of determining the moisture content of a bale of material with multiple layers and a tie bar, including: (a) producing a circularly polarized microwave radiation beam; (b) receiving the source beam as an exit beam with two linearly polarized antennas; (c) conveying the bale between the microwave radiation source and the microwave antenna, such that when the source beam passes through a portion of the bale, the exit beam is received by the microwave antenna, and such that the source beam is enabled to pass through a plurality of portions of the bale; (d) determining an amplitude of each mutually orthogonal component of the exit beam; (e) determining an attenuation of each of the mutually orthogonal components from the amplitude and producing an attenuated signal; (f) determining an alignment of the bale relative to the source of microwave radiation and the antenna, and then alternately producing one of three signals: (i) a leading edge transition signal, after a leading edge of the bale passes the source of microwave radiation; (ii) an alignment signal, after receiving the leading edge transition signal, the alignment signal being the antenna signal during a time interval when the bale is correctly aligned between the source of microwave radiation and the bale; and (iii) a trailing edge transition signal, after a trailing edge of the bale passes the source of microwave radiation; (g) determining a moisture content of ambient air signal after receiving the trailing edge transition signal; (h) filtering the moisture content of ambient air signal from the alignment signal, producing a corrected signal; (i) removing an effect of the source beam contacting the tie bar from the corrected signal, producing a further corrected signal; (j) normalizing the further corrected signal, so that a normalized signal is produced; (k) determining a moisture content of each of the mutually orthogonal components of the normalized signal by comparing the normalized signal to a calibration curve; (l) calculating a ratio of the moisture contents; (m) comparing the ratio to a predetermined constant; and (n) alternately computing a moisture content of the bale directly from the normalized signal, when the ratio is substantially equal to the predetermined constant, and computing a corrected moisture content of the bale when the ratio is not substantially equal to the predetermined constant.

BRIEF DESCRIPTION OF THE DRAWINGS

The invention is herein described, by way of example only, with reference to the accompanying drawings, wherein:

FIG. 3 shows an example of a calibration curve used for calculating the moisture content of the module according to the present invention;

FIGS. 4A and 4B show a phase region curve of a preferred embodiment of the present invention;

DESCRIPTION OF THE PREFERRED EMBODIMENTS

The present invention is of a method and a device which can be used to measure the moisture content of a module of material.

The principles and operation of a method and a device according to the present invention may be better understood with reference to the drawings and the accompanying description.

Figure 1A:
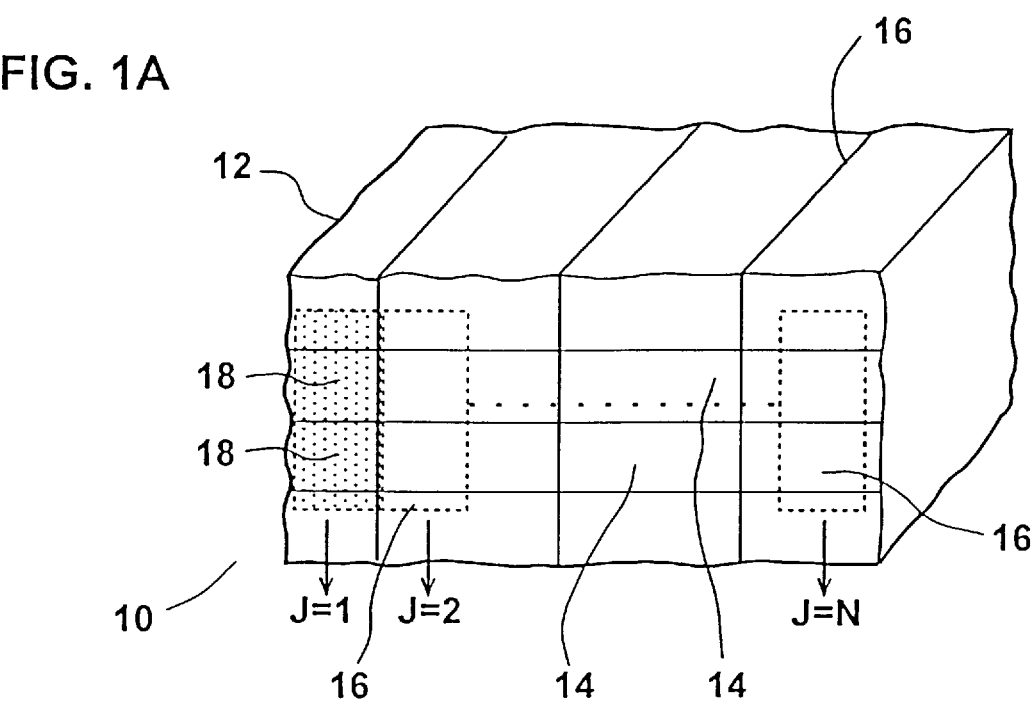
FIGS. 1A and 1B are illustrative examples of modules whose moisture can be measured by the present invention.
Figure 1B:
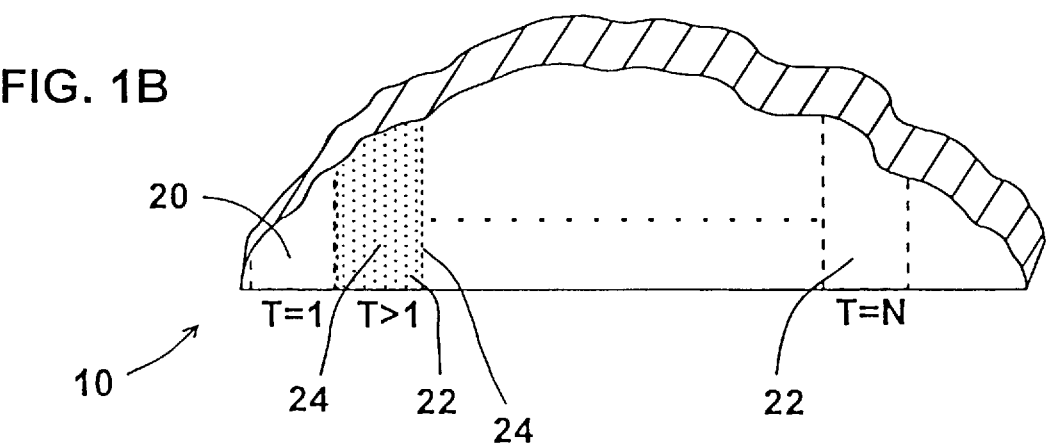

Referring now to the drawings, FIGS. 1A and 1B are illustrative examples of modules whose moisture can be measured by the present invention. FIG. 1A shows a module 10 which is a bale 12. Bale 12 consists of pressed layers of material 14, optionally held together with at least one tie bar 16. Tie bar 16 can be made of plastic or metal. Layers 14 can be any synthetic or organic material, including, but not limited to, tobacco, cotton, paper, processed wood, tea and synthetic fibers. For the purposes of measuring the moisture content of bale 12, bale 12 can be divided into at least one, and preferably a plurality, of areas 16. Each area 16 includes at least one measurement point 18, and preferably a plurality of measurement points 18. At each measurement point 18, the moisture content of that portion of bale 12 is determined (see FIG. 2 below).

FIG. 1B illustrates a module 10 which is a case 20. Case 20 does not have defined layers, unlike bale 12. However, case 20 can also be divided into at least one, and preferably a plurality, of areas 22. Furthermore, each area can also be subdivided into at least one, and preferably a plurality, of measurement points 24. At each measurement point 24, the moisture content of that portion of case 20 is determined (see FIG. 2 below).

Figure 2:
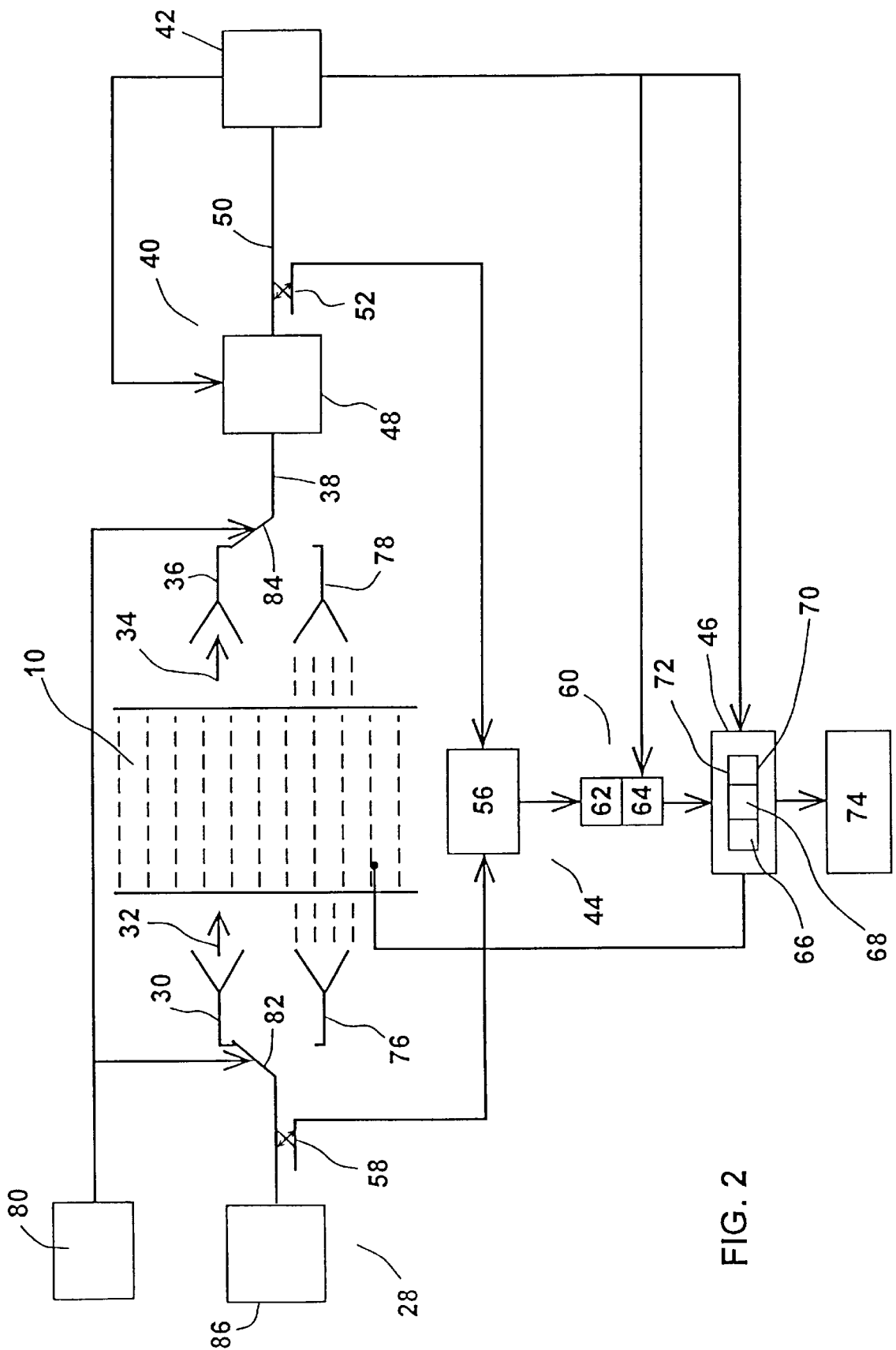
FIG. 2 is a block diagram illustrating one embodiment of the present invention.

FIG. 2 shows a device according to one embodiment of the present invention. Device 26 includes a microwave radiation source 28, shown on one side of module 10. Microwave radiation source 28 preferably includes at least one source antenna 30 for transmitting a source beam 32. Source beam 32 is directed through module 10, and passes out of module 10 as an exit beam 34. Exit beam 34 is received by at least one receiving antenna 36. Receiving antenna 36 is located on a substantially opposing side of module 10 relative to source antenna 30.

After receiving antenna 36 has received exit beam 34, receiving antenna produces an antenna signal 38. Antenna signal 38 then goes to an attenuation unit 40. Attenuation unit 40 includes an attenuation measurer 42, which measures the attenuation of antenna signal 38. As source beam 32 passes through module 10, source beam 32 is attenuated. The extent of this attenuation is determined by the elementary mass, which is the mass of the material of module 10 encountered by source beam 32, and by the moisture content of the material of module 10 encountered by source beam 32. Thus, attenuation measurer 42 is actually measuring the extent to which source beam 32 is attenuated by passing through module 10.

At least a part of antenna signal 38 also goes to a phase shift determiner 44, which determines the phase shift of antenna signal 38. This phase shift is actually the phase shift caused by source beam 32 passing through module 10, so that the phase shift is the difference between the phase of source beam 32 and the phase of exit beam 34. The attenuation and the phase shift are determined according to the following equations:

$$A = 8.68\alpha l$$

l being length of module 10, $\alpha$ being the attenuation factor for module 10.

$$P = (\beta - \beta_0) l$$

$\beta$ and $\beta_0$ being phase factors for module 10 and air, respectively.

The attenuation and the phase shift of antenna signal 38 are then used by a moisture determiner 46 to determine the moisture content of module 10.

Moisture determiner 46 uses the following equations to determine the moisture content of module 10. In these equations, A is attenuation, P is phase shift, W is moisture content, and M is the elementary mass of module 10. Equations 1 and 2 are integrated to produce equations 3 and 4. The moisture content, W, is then calculated.

$$dA = \frac{\partial A}{\partial W} dW + \frac{\partial A}{\partial m} dm$$

$$dP = \frac{\partial P}{\partial W} dW + \frac{\partial P}{\partial m} dm$$

$$A = \frac{\partial A}{\partial W} W + \frac{\partial A}{\partial m} m$$

$$P = \frac{\partial P}{\partial W} W + \frac{\partial P}{\partial m} m$$

A number of optional features can be added to device 26 in order to increase the accuracy of moisture measurements. Preferably, attenuation unit 40 includes an attenuator 48. The function of attenuator 48 is to attenuate antenna signal 38, so that antenna signal 38 becomes an attenuated antenna signal 50. A coupler 52 then splits attenuated antenna signal 38 into two portions. A first portion of attenuated antenna signal 50 goes to phase shift determiner 44. A second portion of attenuated antenna signal 50 preferably goes to attenuation measurer 42. Attenuation measurer 42 preferably determines the difference between the amplitude of attenuated antenna signal 50 and the amplitude of a constant reference signal 54. The difference between these two amplitudes determines the extent to which attenuator 48 attenuates antenna signal 38, so that the attenuation of antenna signal 38 is kept substantially constant. Such constancy is required for the proper operation of phase shift determiner 44 (see below).

As noted above, phase shift determiner 44 determines the difference, or phase shift, between the phase of source beam 32 and the phase of exit beam 34. Phase shift determiner 44 preferably includes a mixer 56, which outputs a signal which is proportional to the phase shift between source beam 32 and exit beam 34, as represented by antenna signal 38. In order for mixer 56 to receive a portion of source beam 32, microwave radiation source 28 preferably includes a second coupler 58, for splitting source beam 32 into two portions. A first portion of source beam 32 is directed through module 10 as described above. A second portion of source beam 32 is directed to mixer 56.

Phase shift determiner 44 preferably also includes a signal phase shift measurer 60. Signal phase shift measurer 60 measures the phase shift between source beam 32 and exit beam 34 from the signal output by mixer 56. In order to obtain the most accurate moisture content measurements, phase shift measurer 60 can optionally include a number of features designed to compensate for inaccuracies in the measurement of the phase shift. These features include a raw phase shift measurer 62, which determines the raw phase shift. Next, a phase region determiner 64 determines the phase region of the raw phase shift from the attenuation of antenna signal 38 and produces a corrected phase shift. As measured directly from source beam 32 and exit beam 34, as represented by antenna signal 38, the phase shift can only vary from 0 to $2\pi$. However, the correct phase actually lies between $2\pi(n-1)$ and $2\pi n$, which can be from 0 to $2\pi$, but which could also be from $4\pi$ to $6\pi$, for example. Thus, the phase region, or the value of n, must be determined. Such a determination is made using an empirical phase region curve, as shown in FIG. 4 below, which relates the attenuation of antenna signal 38 to the phase region. The correct phase shift is then given to moisture determiner 46.

In order for the phase shift measurement to be accurate, the attenuation of antenna signal 38 must be kept substantially constant. Otherwise, the comparison between source beam 32 and antenna signal 38 will be artifactually altered by the attenuation of antenna signal 38.

As noted above, once the phase shift and the attenuation have been measured, moisture determiner 46 determines the moisture content of module 10. Moisture determiner 46 preferably includes a temperature sensor 66 for measuring the temperature of module 10. The type of module 10 is preferably input into moisture determiner 46 by a module type input 68. The type of module 10 is determined by the material of module 10, and by the form of module 10: for example, bale 12 or case 20. Finally, moisture determiner 46 preferably includes a normalizer 70. Normalizer 70 preferably includes an empiric function 72. Empiric function 72 determines the moisture content of module 10 from the temperature and type of module 10, and from the attenuation and phase shift calculated above.

The above description has treated the measurement of the moisture content of module 10 as though a single moisture measurement was made. However, preferably a plurality of such measurements are made and averaged by an averager 74. As described in FIG. 1, bale 12 can be divided into preferably a plurality of areas 16. Each area 16 is preferably subdivided into a plurality of measurement points 18. At each measurement point 18, the moisture content of that portion of bale 12 is determined according to the above description, so that a plurality of measurements are made and averaged by averager 74. A similar argument can be made for case 20, areas 22 and measurement points 24. These averaged measurements are then preferably compared to a calibration curve, of the type shown in FIG. 3, in order to obtain the moisture content of module 10. Optionally, in order to facilitate such multiple measurements, device 26 can include a conveyor, such as a conveyor belt (not shown) or a truck (not shown, see FIG. 6) to convey bale 12 between microwave radiation source 28 and receiving antenna 36.

Optionally, microwave radiation source 28 can also include a second source antenna 76. Also optionally, device 26 can also include a second receiving antenna 78. Optionally, an oscillator 80 controls a first switch 82 and a second switch 84. These optional features are used to measure the moisture content of module 10 in two parts when module 10 is too tall for a single measurement. First, oscillator 80 flips first switch 82 so that first source antenna 30 directs source beam 32, and second switch 84 so that first receiving antenna 36 produces antenna signal 38. This particular configuration is shown in FIG. 2, and is used to measure the moisture content of the lower portion of module 10. Next, oscillator 80 flips first switch 82 so that second source antenna 78 directs source beam 32. Oscillator 80 also flips second switch 84 so that second receiving antenna 78 produces antenna signal 38. Now, the moisture content of the upper portion of module 10 is measured.

Microwave radiation source 28 can also optionally include a number of features which are designed to maximize the sensitivity of the moisture content measurements, by manipulating the direction of the electric field density of source beam 32 (see also FIGS. 5A–5F). Microwave radiation source 28 can include an electric field director 86. Electric field director 86 determines a direction of the electric field density of source beam 32 relative to module 10, such that the direction of the electric field density partially determines the magnitude of the attenuation and the magnitude of the phase shift. If module 10 has layers 14 (not shown), substantially the maximum attenuation and substantially the maximum phase shift of antenna signal 38 is obtained when the electric field density is substantially perpendicular to layers 14 (not shown) of module 10. When the electric field density is substantially parallel to layers 14 (not shown) of module 10, substantially the minimum attenuation and the minimum phase shift of antenna signal 38 is obtained. Even if module 10 does not have layers 14, changing the direction of the electric field density will still alter the attenuation and phase shift of antenna signal 38, according to the orientation of the material being measured relative to the electric field density. Electric field director 86 determines the direction of the electric field density according to feedback from attenuation measurer 42. Thus, if the attenuation of antenna signal 38 is low, electric field director 86 can change the direction of the electric field density in order to compensate. Clearly, this has obvious advantages in maximizing the sensitivity and accuracy of the moisture measurements.

FIG. 3 shows an illustrative example of a calibration curve 88, showing the relationship between attenuation, in dB, on the Y-axis, and moisture content, as a percentage, on the X-axis. Each calibration curve 88 is empirically determined for each type of module 10 (for example bale or case), and for each type of material (for example, cotton or tobacco). The moisture content of module 10 is then determined from calibration curve 88. A more complete description of these curves and their derivation can be found in "Theoretical and Experimental Investigation of Microwave Moisture Measurement of Materials" by A. Greenwald, FAN, Uzbekistan, 1982.

FIG. 4A shows a graph of a phase region curve 90 as mentioned above. Phase region curve 90 is an empirical curve of the attenuation of antenna signal 38 on the X-axis, and the phase region on the Y-axis. As an example, if the attenuation is equal to Al, phase region curve 90 shows that the phase region lies between 0 and $2\pi$. Different phase region curves must be determined for each material and type of module 10.

In order to use this curve, the attenuation and phase shift of antenna signal 38 are preferably measured as module 10 is conveyed between source antenna 30 and receiving antenna 36. For example, a first measurement could be made before the leading edge of module 10 enters the region between source antenna 30 and receiving antenna 36, a second measurement could be made as the leading edge of module 10 enters that region, and a third measurement could be made when module 10 is aligned between source antenna 30 and receiving antenna 36. The relationship between these multiple measurements and the phase region is shown in FIG. 4B. At the top is a diagram of module 10 being conveyed between source antenna 30 and receiving antenna 36. At the bottom is a graph of the relationship between the increasing attenuation as module 10 becomes aligned between source antenna 30 and receiving antenna 36, and the phase shift, which is based upon empirical phase region curve 90 of FIG. 4A. As the phase shift cycles between 0–2π while module 10 is conveyed between source antenna 30 and receiving antenna 36, the number of cycles can be counted and the phase region can be determined.

Figure 5A:
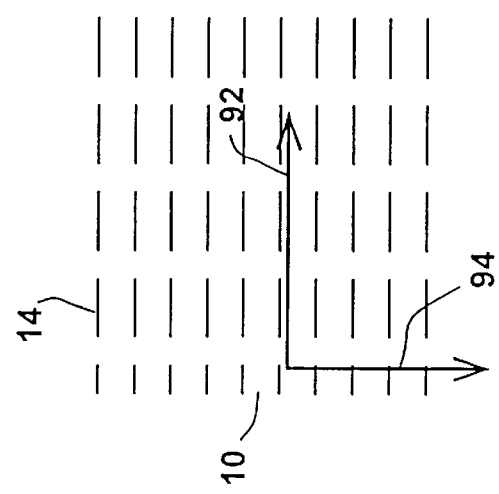
FIGS. 5A–5F illustrate the relationship between the direction of the electrical field of the source beam relative to the module and the attenuation and phase shift of the antenna signal.
Figure 5B:
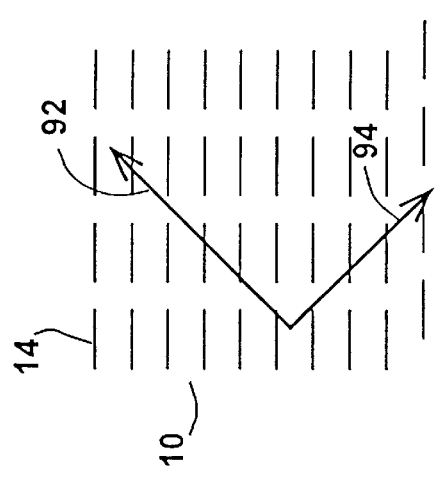
Figure 5C:
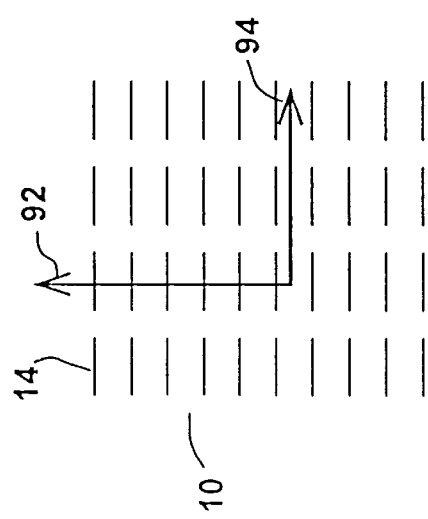
Figure 5D:
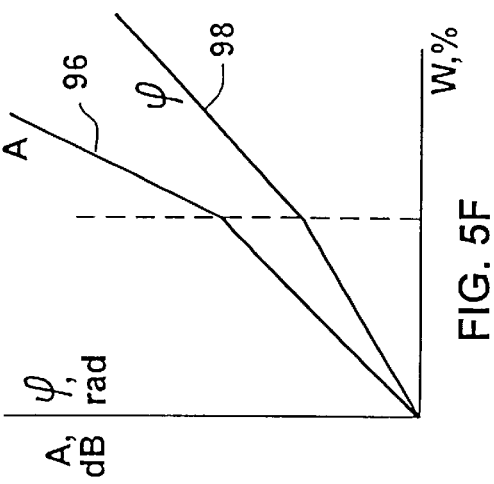
Figure 5E:
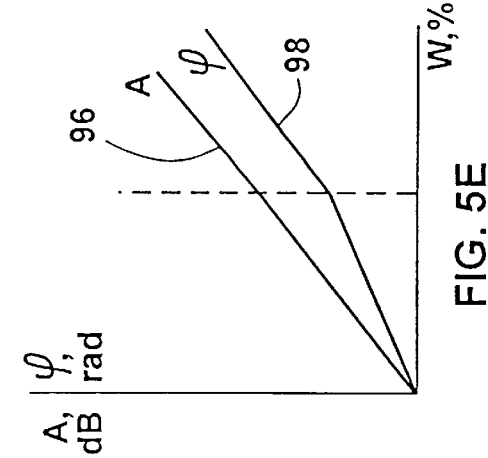
Figure 5F:
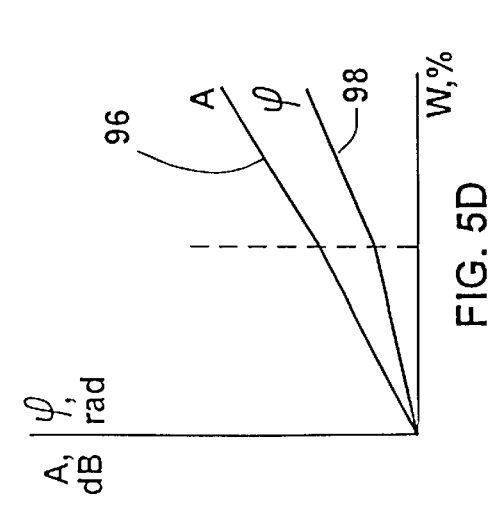

FIGS. 5A–5F illustrate the relationship between the direction of the electric field density of the source beam relative to the module and the attenuation and phase shift of the antenna signal. FIG. 5A shows an electric field density 92 and a magnetic field density 94. Electric field density 92 is perpendicular to layers 14 of module 10. In FIG. 5B, electric field density 92 has been rotated by about 45 degrees. In FIG. 5C, electric field density 92 has been rotated by about 90 degrees, relative to FIG. 5A. Now electric field density 92 is parallel to layers 14 of module 10. FIGS. 5D–5F show the effect of these shifts in the direction of electric field density 92 on attenuation 96 and phase shift 98 of antenna signal 38. In FIG. 5D, both attenuation 96 and phase shift 98 of antenna signal 38 are at substantially a minimum level, because electric field density 92 is perpendicular to layers 14, as shown in FIG. 5A. In FIG. 5E, both attenuation 96 and phase shift 98 of antenna signal 38 have increased, due to the rotation of electric field density 92 as shown in FIG. 5B. Finally, in FIG. 5F, both attenuation 96 and phase shift 98 of antenna signal 38 are at substantially a maximum level, because electric field density 92 is parallel to layers 14, as shown in FIG. 5C.

Figure 6:
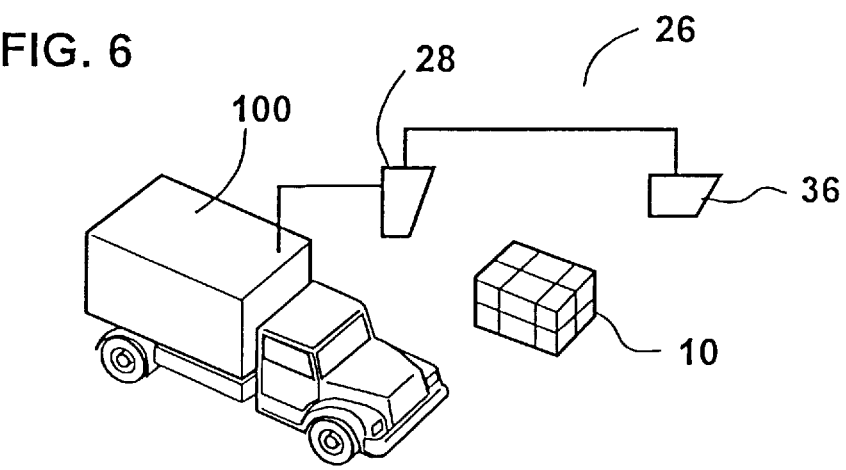
FIG. 6 illustrates a truck for conveying the device of FIG. 2.

Optionally, device 26 can be mounted on a truck 100, as shown in FIG. 6. Microwave radiation source 28 and receiving antenna 36 are both mounted on truck 100. Truck 100 then moves past module 10, so that module 10 passes between microwave radiation source 28 and receiving antenna 36. In this manner, a plurality of moisture measurements of module 10 can be made and averaged, as described above.

Figure 7A:
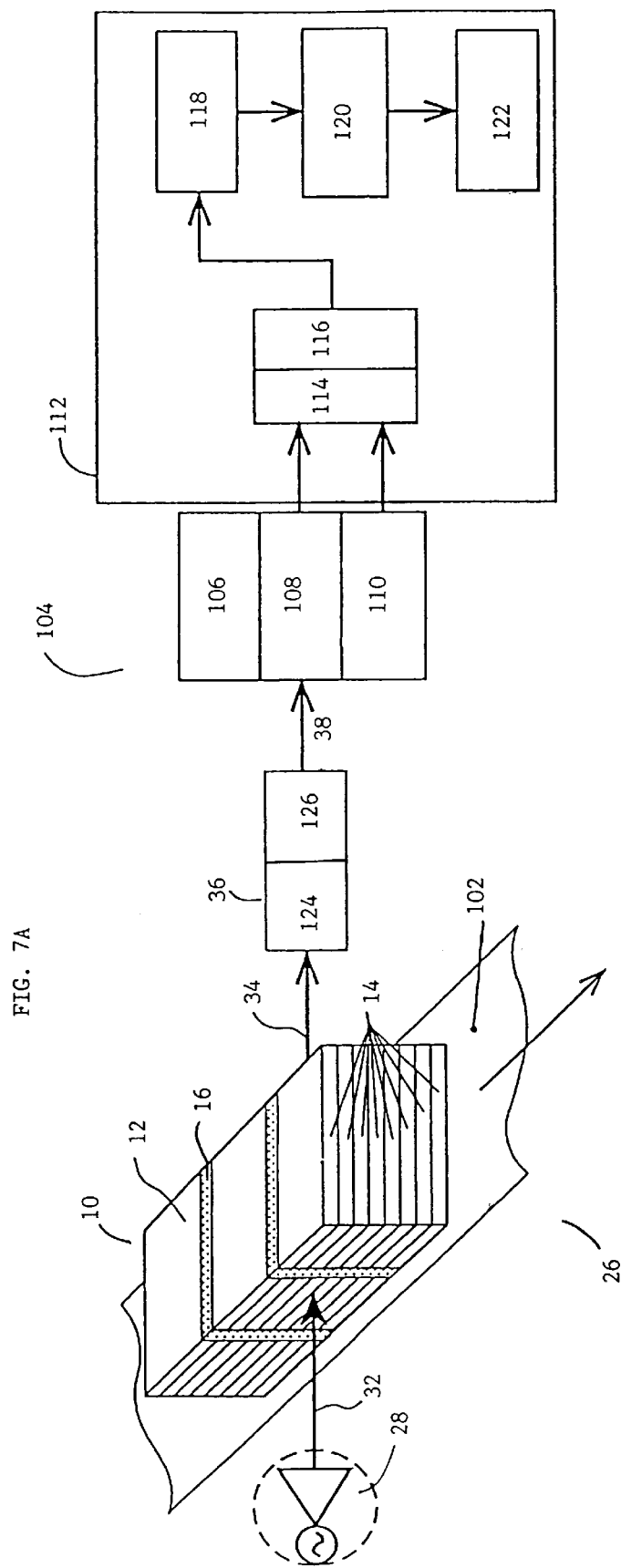
FIGS. 7A–7C illustrate another embodiment of the present invention.
Figure 7B:
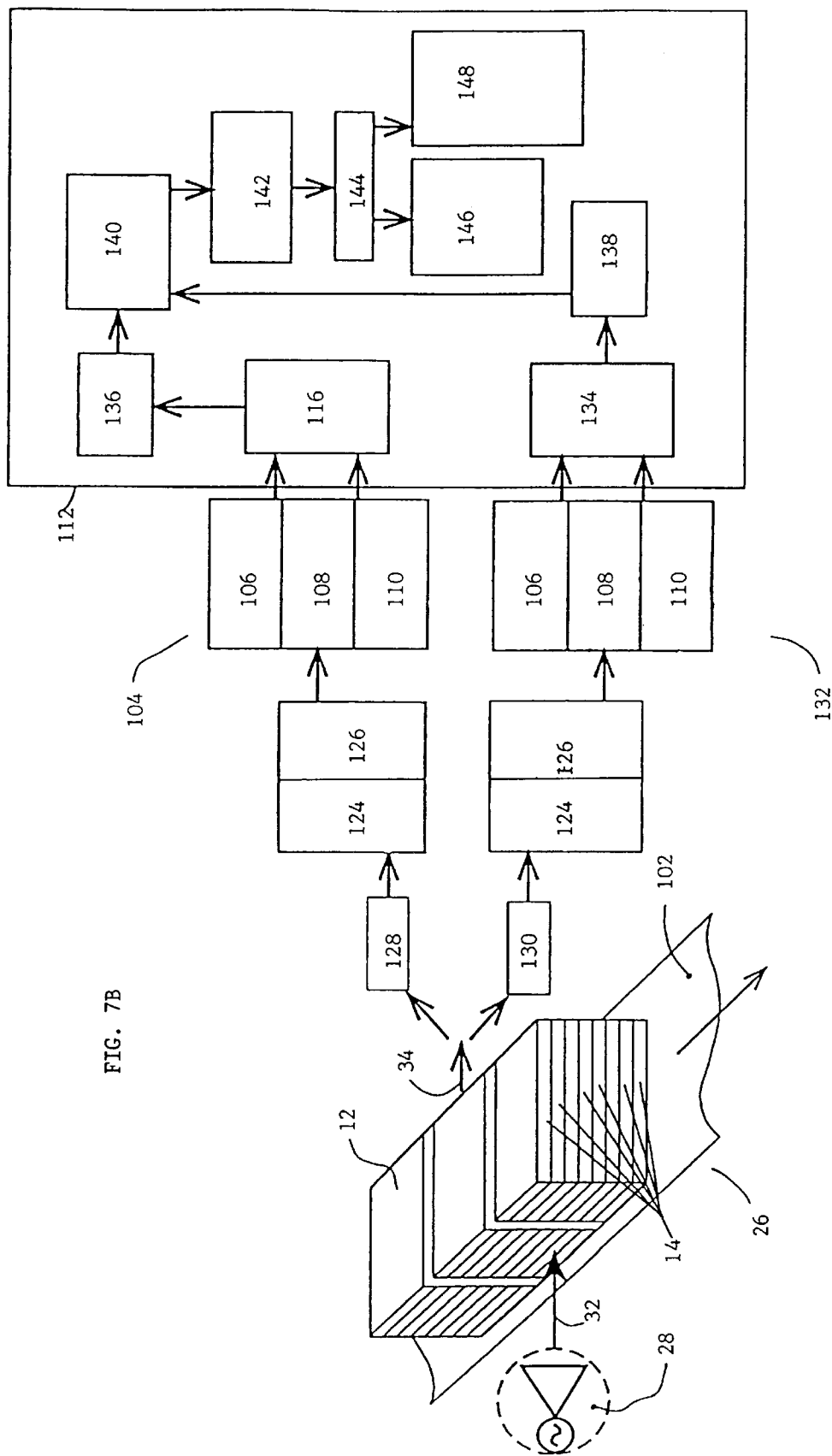
Figure 7C:
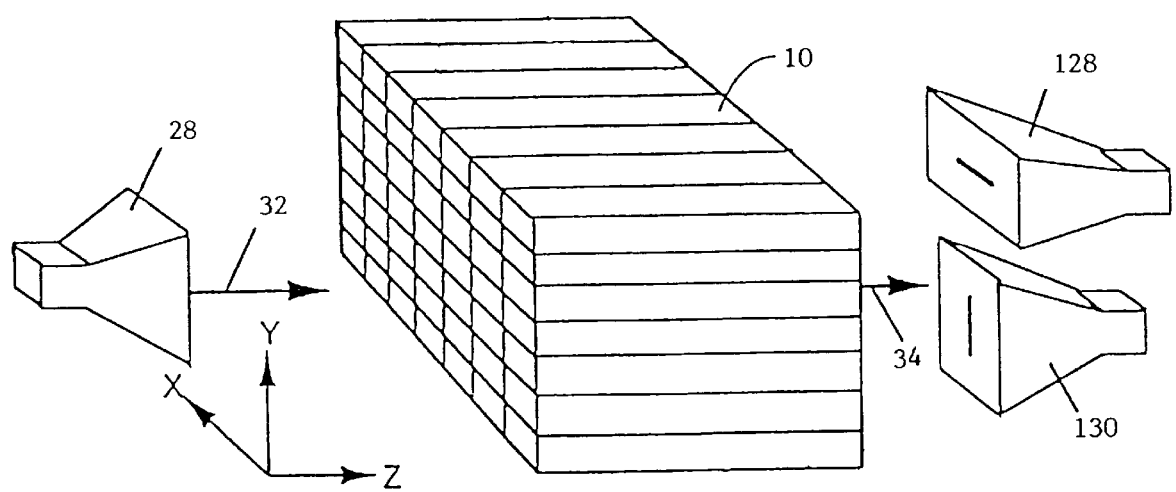

FIGS. 7A–7C illustrate another embodiment of the present invention. FIG. 7A is a schematic illustration of another embodiment of device 26, similar to the one shown in FIG. 2, except that receiving antenna 36 is preferably a circularly polarized antenna. Furthermore, a conveyor 102, such as a conveyor belt, moves module 10, shown here as bale 12, between source of microwave radiation 28 and receiving antenna 36, such that source beam 32 passes through a portion of bale 12, and exits bale 12 as an exit beam 34. Since conveyor 102 is moving module 10, source beam 32 can pass through a plurality of portions of bale 12. Thus, if there are i such portions along bale 12, i moisture measurements can be made. Exit beam 34 is received by receiving antenna 36, which then produces an antenna signal 38.

In this embodiment, antenna signal 38 is then examined by a bale alignment determiner 104. Bale alignment determiner 104 then determines the alignment of bale 12 relative to source beam 32 and receiving antenna 36. Bale alignment determiner 104 includes a leading edge transition determiner 106, an interval timer 108 and a trailing edge transition determiner 110. Leading edge transition determiner 106 detects when a leading edge of bale 12 has passed radiation source 28, and produces a leading edge transition signal. Interval timer 108 receives the leading edge transition signal and produces an alignment signal, such that alignment signal is produced when bale 12 is correctly aligned between microwave radiation source 28 and receiving antenna 36. Trailing edge transition determiner 110 determines when the trailing edge of bale 12 passes microwave radiation source 28, and produces a trailing edge transition signal.

A moisture determiner 112 then determines the moisture content of bale 12 from the alignment signal. Moisture determiner 112 includes a background moisture content measurer 114, which measures the background moisture content of antenna signal 38 after receiving the trailing edge transition signal. This background moisture content includes both the ambient moisture content, from source beam 32 passing through the air, and artifacts caused by device 26 itself, such as misalignment of source beam 32 relative to bale 12 and movement of receiving antenna 36 from the correct position relative to bale 12. Moisture determiner 112 also includes a filter 116 for producing a corrected signal by removing the background moisture content from the alignment signal.

Preferably, moisture determiner 112 also includes a tie bar suppressor 118. If source beam 32 contacts a tie bar 16 as source beam 32 goes through bale 12, antenna signal 38 can be affected, potentially resulting in an incorrect moisture measurement. Tie bar suppressor 118 removes any such effects from the corrected signal, and produces a further corrected signal. Preferably, this corrected signal then goes to a normalizer 120. Normalizer 120 compensates for effects caused by temperature, mass and length of bale 12, thus normalizing the corrected signal. Such normalization is performed by the following equations:

$W_{X_i}$=the $i^{th}$ moisture measurement in the X-channel, $W_{Y_i}$=the $i^{th}$ moisture measurement in the Y-channel, $W_0$=the nominal mass of the bale ≈250 Kg, $W_c$=the actual measured mass of the bale, $L_0$=the nominal length of the layers taken along the width of the bale, $L_c$=the actual length of the layers taken along the width of the bale, $T_o$=the base temperature of the cotton fibers (35° C.) an $T_c$=the temperature of the cotton fibers in the current slice, it may be shown that:

$$W_{x_i'} = \frac{T_o - T_c}{10} + W_{x_i}$$

$$W_{y_i'} = \frac{T_o - T_c}{10} + W_{y_i}$$

$$W_{x_i''} = W_{x_i'} \cdot \frac{(W_o)}{W_c}$$

$$W_{y_i''} = W_{x_i'} \cdot \frac{(W_o)}{W_c}$$

$$W_{x_i'''} = W_{x_i''} \cdot \frac{(L_o)}{L_c}$$

-continued $$W_{y_i^m} = W_{x_i^n} \cdot \frac{(L_o)}{L_c}$$

Finally, the normalized signal preferably goes to a mean moisture unit 122, which determines the moisture content of bale 12. Preferably, mean moisture unit 122 averages the moisture content of bale 12 over all i measurements of i portions of bale 12.

Receiving antenna 36 can optionally include an amplitude determiner 124 and an attenuation determiner 126. Amplitude determiner 124 determines an amplitude of exit beam 34. Attenuation determiner 126 then produces an attenuated signal, by determining an attenuation of exit beam 34 from the amplitude of exit beam 34. The attenuated antenna signal is then processed in a similar fashion as antenna signal 38.

In the preferred embodiment shown in FIG. 7B, source beam 32 is circularly polarized, and exit beam 34 has two mutually orthogonal components. One of these components is in the direction of the X-axis, and one component is in the direction of the Y-axis. For convenience, FIG. 7C shows a partial illustration of device 26 according to FIG. 7B, with X-, Y- and Z-axes illustrated.

Referring back to FIG. 7B, each component is received by one of two linearly polarized microwave receiving antennas 128 and 130, respectively. Each mutually orthogonal component is separately processed, similar to the above description in FIG. 7A, so that there are two bale alignment determiners 104 and 132. Moisture determiner 112 has two filters 116 and 134 for removing the background moisture component and producing a corrected signal. Preferably, two digital samplers 136 and 138 then produce a digitized signal from each component of the corrected signal. There is also preferably a component moisture computer 140 which then computes a moisture content of each mutually orthogonal component of the digitized signal.

Preferably, moisture determiner 112 also has a ratio determination unit 142 for determining a ratio of each of the moisture contents produced by component moisture computer 140, according to the following equations:

$$W_{i_{x(meas)}} = W_{i_x} \cos\beta + W_{i_y} \sin\beta$$

$$W_{i_{y(meas)}} = W_{i_x} \sin\beta + W_{i_y} \cos\beta$$

$$K = W_{i_x}/W_{i_y}$$

where:

$W_{i_{x(meas)}}$=measured moisture content in the X direction for the $i^{th}$ area, $W_{i_{y(meas)}}$=measured moisture content in the Y direction for the $i^{th}$ area, $W_{i_x}$=maximum moisture content of the $i^{th}$ area in the X-direction, $W_{i_y}$=maximum moisture content of the $i^{th}$ area in the Y-direction, $\beta$=the angle of inclination of the layers to the X-direction, K=the ratio of the maximum moisture values in the X and Y directions, and $\alpha_i$=the measured ratio $W_{i_{x(meas)}}:W_{i_{y(meas)}}$.

A comparator 144 then compares the ratio with the predetermined constant K, which is obtained when layers in bale 12 are substantially parallel. If the ratio is substantially equal to K, a parallel layer moisture determiner 146 determines the moisture content of bale 12. Otherwise, a non-parallel layer moisture determiner 148 determines the moisture content of bale 12 when the ratio is substantially not equal to the predetermined constant K.

Non-parallel layer moisture determiner 148 preferably determines the moisture content of bale 12 by using an empirical function $$W = W_y + 3.2 \times 10^{-2} \frac{(\alpha - 1)}{K}$$

where W is the moisture content of the signal, $W_Y$ is the moisture content of one of the mutually orthogonal components which passed through bale 12 in a direction normal to layers, $\alpha$ is the ratio, and K is the predetermined constant.

Figure 8:
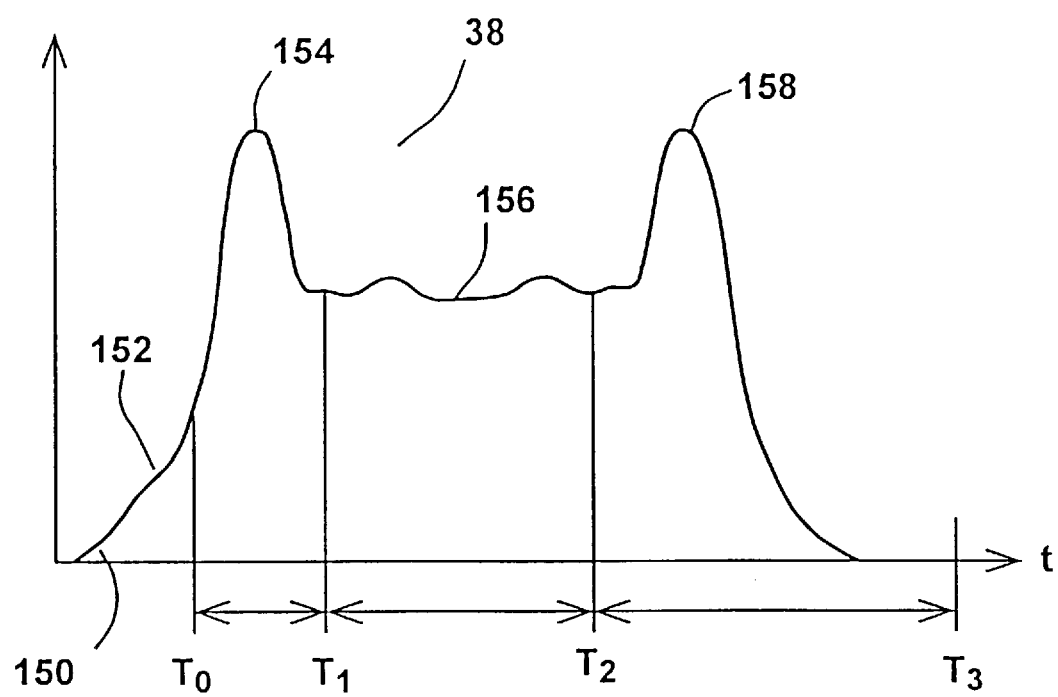
FIG. 8 illustrates the behavior of the antenna signal of the embodiment of FIGS. 7A and 7B.

FIG. 8 illustrates the behavior of the antenna signal of the embodiment of FIGS. 7A and 7B. Antenna signal 38 starts at a generally low background level 150 which climbs to an initial higher level 152 at a time $T_0$ when bale 12 (not shown) enters the region between microwave radiation source 28 (not shown) and receiving antenna 36 (not shown). Antenna signal 38 then reaches a first artifactual peak 154 during time interval $T_1$, due to edge transition effects caused by the leading edge of bale 12 passing between microwave radiation source 28 (not shown) and receiving antenna 36 (not shown). During this time, a first portion of source beam 32 passes through bale 12 (not shown), and a second portion does not, causing these edge transition effects.

Once bale 12 (not shown) is correctly aligned between microwave radiation source 28 (not shown) and receiving antenna 36 (not shown), for example as in FIGS. 7A and 7B, antenna signal 38 goes to a steady level 156 during time interval $T_2$ and remains substantially constant during this time interval, except for fluctuations due to local inequalities in the moisture content and structure of bale 12. During time interval $T_2$, the alignment signal is produced, and all moisture measurements of bale 12 are made. At time $T_3$, the trailing edge of bale 12 (not shown) starts to move past microwave radiation source 28 (not shown) and receiving antenna 36 (not shown), causing a second artifactual peak 158, again due to edge transition effects caused by the trailing edge of bale 12.

While the invention has been described with respect to a limited number of embodiments, it will be appreciated that many variations, modifications and other applications of the invention may be made.

What is claimed is:

1. A device for measuring the moisture content of a module of material, the module featuring a structure, the device comprising:

(a) a source of microwave radiation for producing a microwave radiation source beam, at least a portion of said source being located on one side of the module, such that at least a portion of said source beam is able to pass substantially completely through a portion of the module to form a passed source beam;

(b) at least one microwave antenna located on an opposing side of the module, said antenna being spatially separated from said source such that said source beam must travel on a path selected from the group consisting of through the module and across the module, said antenna receiving an exit beam and said antenna producing an antenna signal, said exit beam being said source beam after a transition from said source to said antenna, such that at least a portion of said exit beam is said passed source beam;

(c) a conveyor for conveying the module between said source and said antenna, such that a plurality of antenna signals, a plurality of source beams and a plurality of exit beams are produced;

(d) an attenuation unit for receiving a first portion of each of said plurality of antenna signals and for measuring an attenuation of each of said plurality of antenna signals;

(e) a phase shift determiner for receiving a portion of each of said plurality of said source beams and a second portion of each of said plurality of antenna signals and for determining a phase shift between each of said plurality of said source beams and each of said plurality of antenna signals, said phase shift determiner including:

(i) a raw phase shift measurer for determining a raw phase shift of each of said plurality of said source beams and each of said plurality of antenna signals; and (ii) a phase region determiner for determining a phase region of said raw phase shift from said attenuation of each of said plurality of said antenna signals and from an empirical curve determined for the structure of the module and the type of material, said empirical curve showing a relationship between said attenuation and said phase region, said phase region having a value in a range of from $2\pi(n-1)$ to $2\pi n$, n being determined by counting a number of cycles of said raw phase shift as the module is conveyed between said source antenna and said receiving antenna, such that said phase region determiner is able to produce a corrected phase shift according to said value of n; and (e) a moisture determiner for determining a moisture content of the module from said corrected phase shift and said attenuation.

2. The device of claim 1, wherein said attenuation unit further includes:

(a) an attenuation measurer for measuring an amplitude of said antenna signal, for comparing said attenuation to an amplitude of a reference signal of a constant amplitude, and for determining a difference between said constant amplitude of said reference signal and said amplitude of said antenna signal; and (b) an attenuator for attenuating said antenna signal according to said difference.

3. The device of claim 1, wherein said phase region determiner further includes an empirical curve for determining said phase region from said attenuation, said phase region having a value in a range of from $2\pi(n-1)$ to $2\pi n$, such that said phase region determiner is able to determine a value for n from said empirical curve and from said attenuation.

4. The device of claim 1, wherein:

(a) said microwave radiation source further includes;

(i) a first source antenna for producing and focussing said source beam such that said source beam passes through a lower portion of the module;

(ii) a second source antenna for producing and focusing said source beam such that said source beam passes through a lower portion of the module, and (b) said at least one receiving antenna is a first receiving antenna and a second receiving antenna, and said receiving antenna includes a switch, such that said first receiving antenna produces said antenna signal when said first source antenna produces and focusses said source beam, and said second receiving antenna produces and focusses said antenna signal when said second source antenna produces and focusses said source beam.

5. The device of claim 1, wherein said microwave radiation source further includes an electric field director for manipulating a direction of an electric field of said source beam relative to the module, such that said direction of said electric field at least partially causes a magnitude of said attenuation and a magnitude of said phase shift.

6. The device of claim 1, wherein said moisture determiner further includes:

(a) a temperature sensor for determining a temperature of the module;

(b) a module type input for inputting a type of the module; and (c) a normalizer for determining the moisture content from said temperature, said type, said corrected phase shift and said attenuation.

7. The device of claim 1, further including:

(a) a conveyor for conveying the module, such that multiple moisture measurements are made; and (b) an averager for averaging said multiple moisture measurements.

8. The device of claim 1, wherein the material in the module has a substantially irregular structure.

9. The device of claim 1, wherein said phase shift determiner receives a plurality of portions of said source beam and a plurality of portions of said antenna signal, such that said phase region of said raw phase shift is determined by counting a number of phase shift cycles, each phase shift cycle including values of said raw phase shift in a range from 0 to $2\pi$.

10. The device of claim 1, wherein the module is selected from the group consisting of bale and case, and the structure of the material is substantially irregular.

11. The device of claim 1, wherein the module is selected from the group consisting of a bale and a case.

12. The device of claim 11, wherein the module is said bale and the material is selected from the group consisting of tobacco, cotton, paper, processed wood, tea and synthetic fibers.

13. The device of claim 11, wherein the module is said case and the material is selected from the group consisting of cotton, tobacco, tea and synthetic fibers.

* * * * *